US006575990B1

(12) United States Patent
Wang et al.

(10) Patent No.: US 6,575,990 B1
(45) Date of Patent: Jun. 10, 2003

(54) HIGH SPEED VITREOUS CUTTING SYSTEM

(75) Inventors: Carl C. Wang, Oakland, CA (US); Erik W. Peterson, Walnut Creek, CA (US)

(73) Assignee: Medical Instrument Development Laboratories, Inc., San Leandro, CA (US)

( * ) Notice: Subject to any disclaimer, the term of this patent is extended or adjusted under 35 U.S.C. 154(b) by 158 days.

(21) Appl. No.: 09/693,107

(22) Filed: Oct. 20, 2000

Related U.S. Application Data

(60) Provisional application No. 60/160,727, filed on Oct. 21, 1999.

(51) Int. Cl.[7] .............................................. A61B 17/32
(52) U.S. Cl. ..................................................... 606/171
(58) Field of Search ........................... 137/102; 604/22, 604/143; 606/167, 170, 171

(56) References Cited

U.S. PATENT DOCUMENTS

| 3,776,238 A | * | 12/1973 | Peyman et al. ............... 294/15 |
| 3,815,604 A | | 6/1974 | O'Malley et al. |
| 3,884,238 A | | 5/1975 | O'Malley et al. |
| 4,530,359 A | * | 7/1985 | Helfgott et al. ................ 30/362 |
| 4,590,935 A | * | 5/1986 | Ranalli .......................... 604/22 |
| 4,696,298 A | * | 9/1987 | Higgins et al. ................ 604/22 |
| 5,176,628 A | | 1/1993 | Charles et al. |
| 5,284,472 A | * | 2/1994 | Sussman et al. .............. 604/22 |
| 5,547,473 A | * | 8/1996 | Peyman ......................... 604/22 |
| 5,843,111 A | * | 12/1998 | Vijfvinkel ..................... 604/22 |
| 5,979,494 A | * | 11/1999 | Perkins et al. ............... 137/102 |

* cited by examiner

Primary Examiner—Kevin T. Truong
Assistant Examiner—Victor Nguyen
(74) Attorney, Agent, or Firm—Michael Best & Friedrich LLP

(57) ABSTRACT

A high-speed pneumatic cutting system having a cutter and an actuator. The cutter is a guillotine-type, pneumatic cutter that receives a train of pressure pulses from the actuator. The actuator is designed to capture pressure pulses it receives from a pneumatic energy source in a surgical machine, such as a vitrectomy machine, or to generate its own pneumatic energy. The actuator has an accumulator coupled to the outlet of the pneumatic energy and a pressure transducer that senses the pressure level inside the accumulator. A control and display unit with a plurality of input mechanisms receives inputs from a user who selects a desired cutting rate or frequency for the cutter. The control and display unit produces an output signal based on the inputs received. The outputs from the control and display unit and the pressure transducer are sent to a waveform shaping circuit. The waveform shaping circuit produces a command signal based on the inputs that it receives. The command signal is delivered to a valve that is coupled in fluid communication to the accumulator. The valve is opened and closed according to the command signal to produce a pulse train that will operate the cutter at the selected cutting rate. The actuator may be designed as a stand-alone unit or may be integrated into a surgical machine.

37 Claims, 14 Drawing Sheets

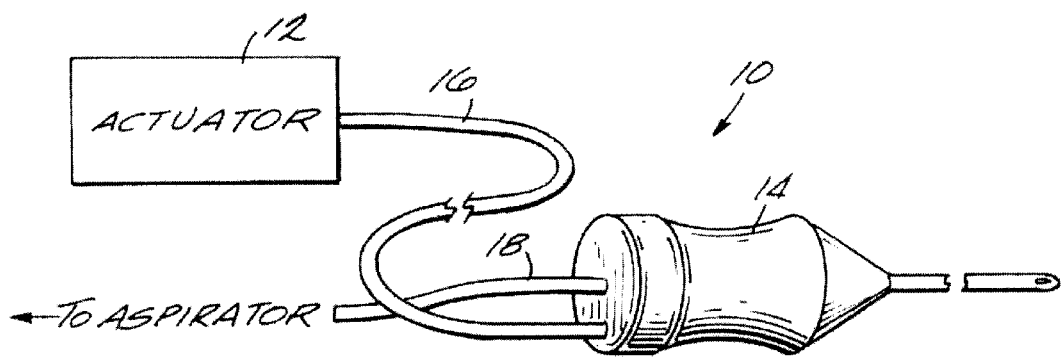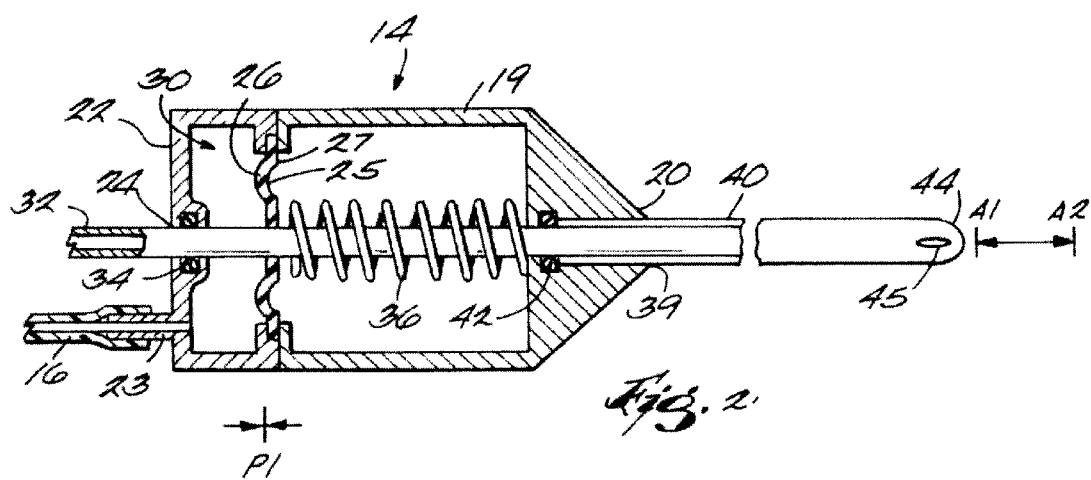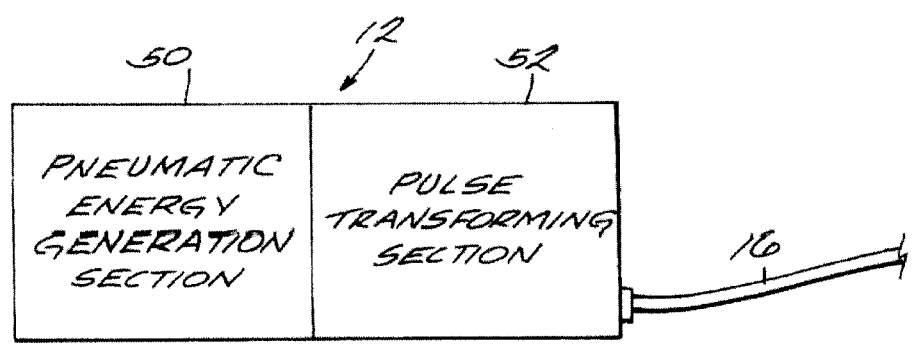

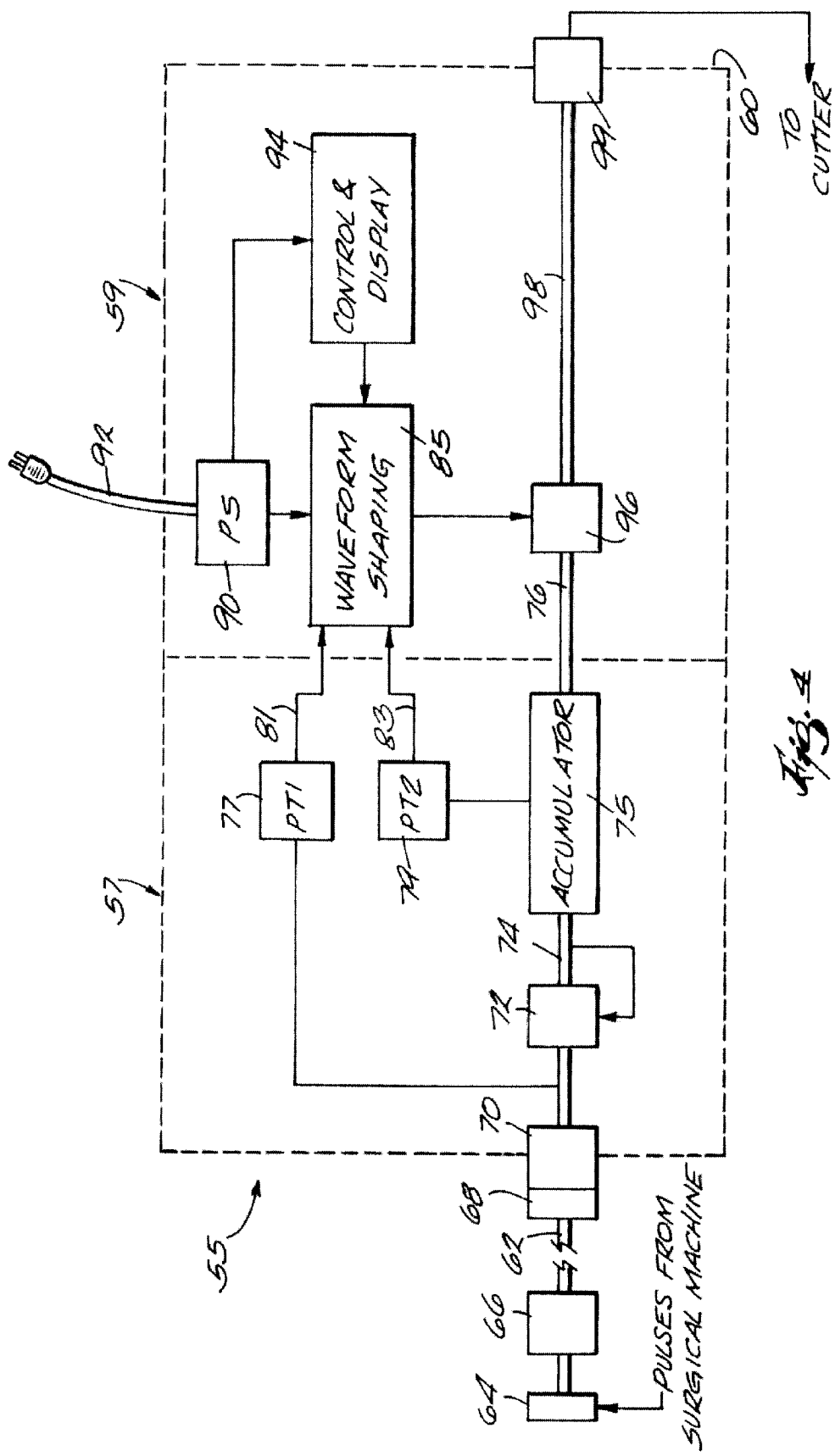

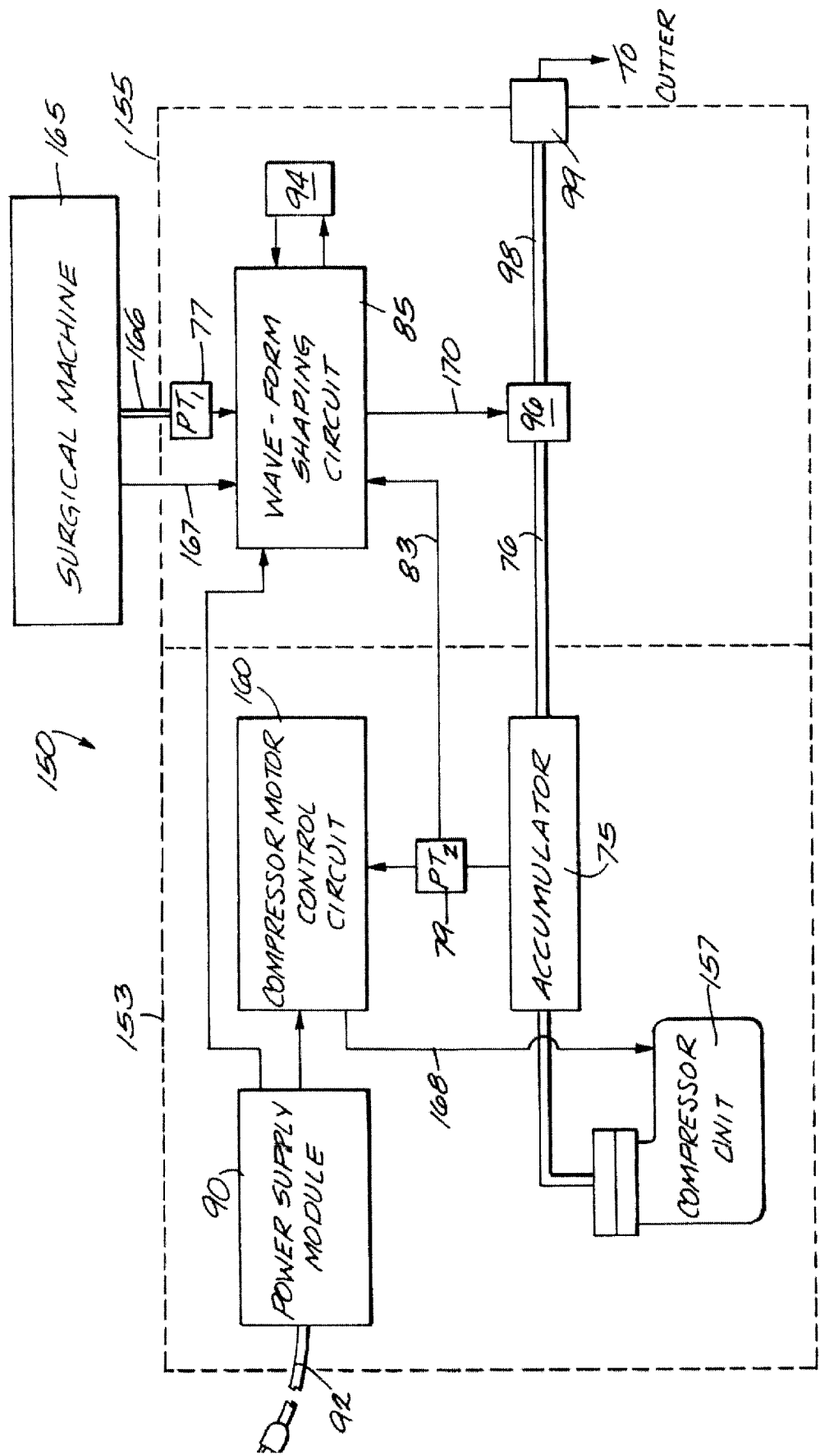

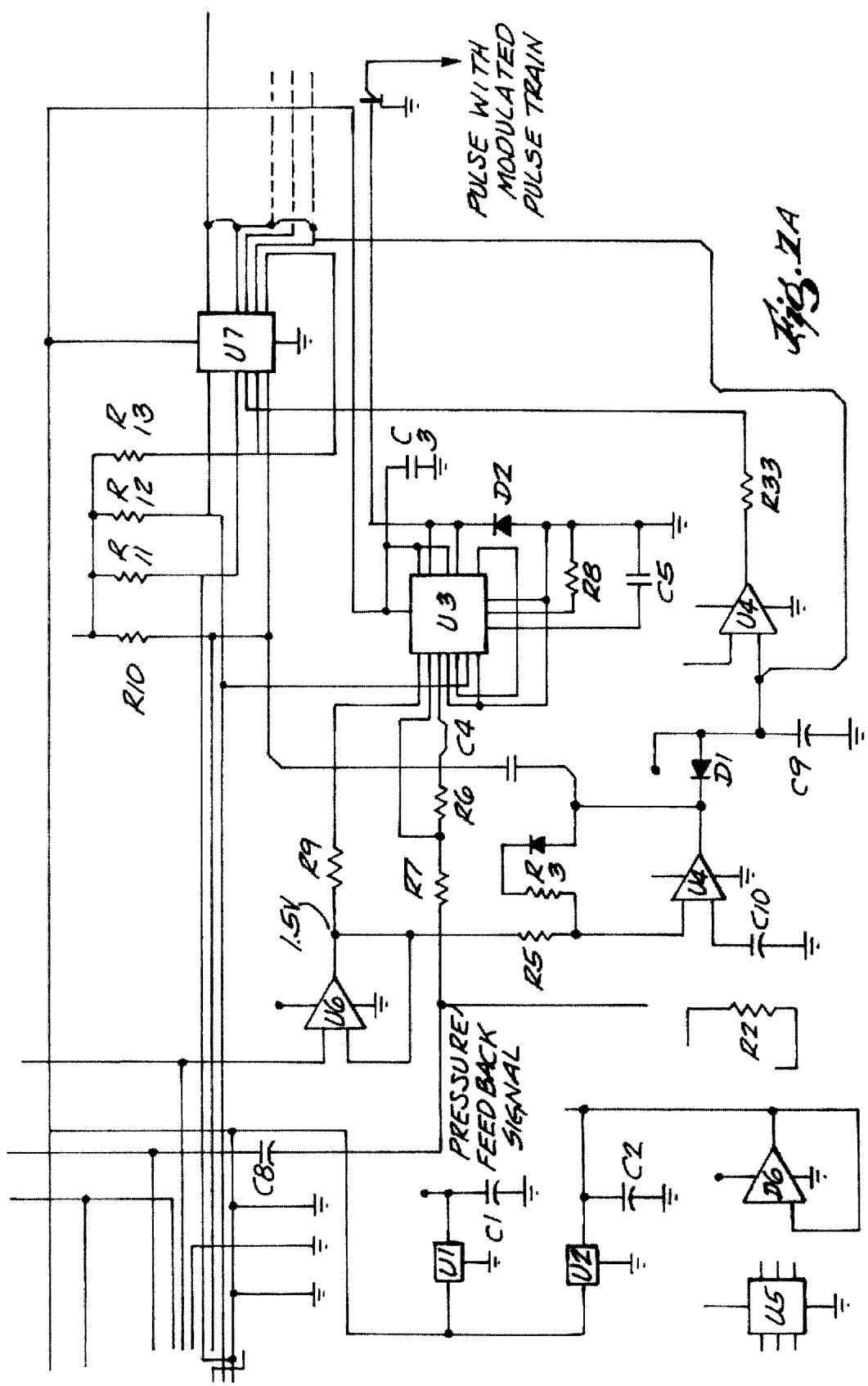

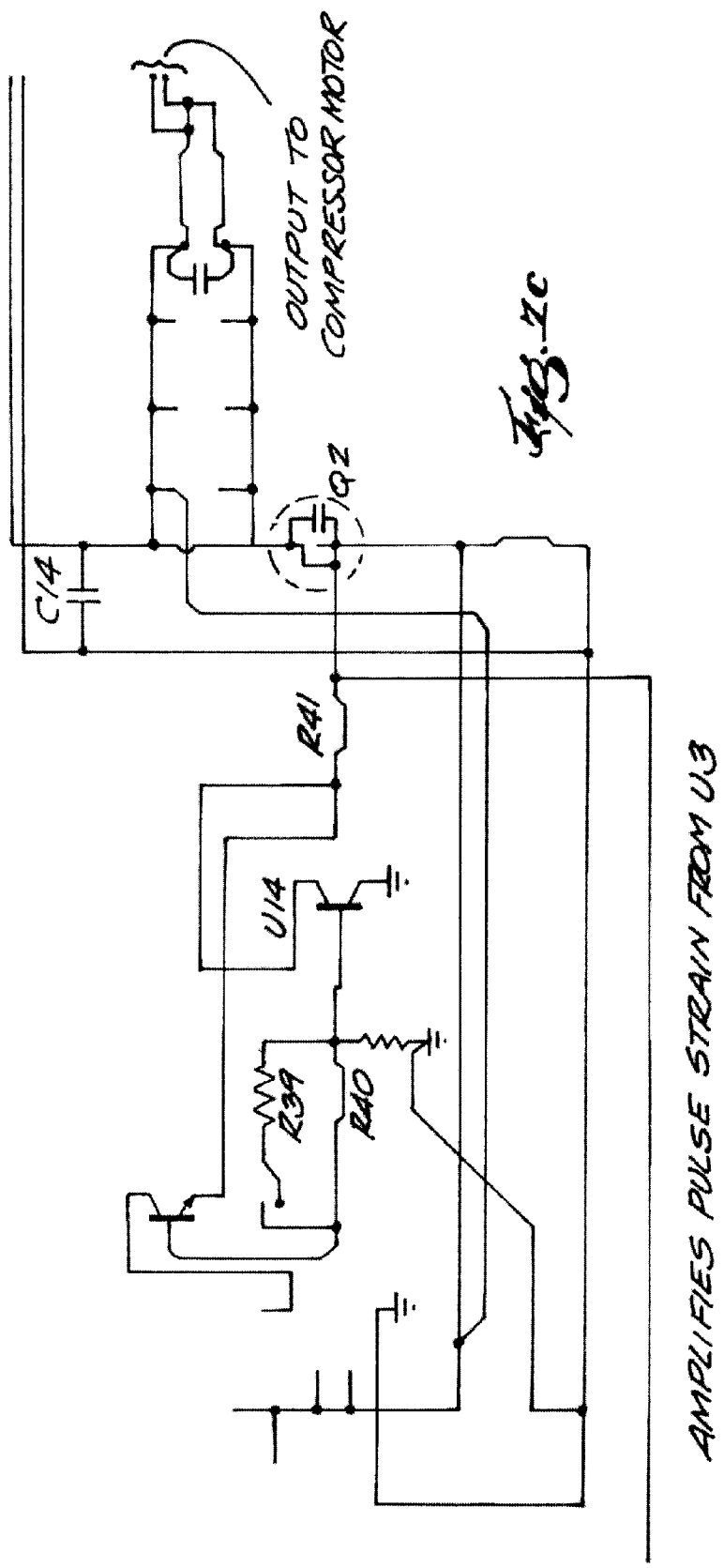

HIGH SPEED VITREOUS CUTTING SYSTEM

RELATED APPLICATIONS

This application claims the benefit of U.S. Provisional Application No. 60/160,727 filed Oct. 21, 1999.

FIELD OF INVENTION

The present invention relates to devices for performing micro-surgical procedures in the posterior portion of the eye. More particularly, the present invention relates to a high-speed pneumatically driven vitreous cutter.

BACKGROUND OF THE INVENTION

The instrument most commonly used, and generally preferred, for vitreous surgery is a pneumatically-operated axial guillotine cutter. A typical pneumatically-operated guillotine cutter has a handpiece that includes a needle with a cutting/aspiration port located near the needle's distal end. The handpiece receives pneumatic power from a vitreoretinal surgical system (or console). Often, the system also provides aspiration and illumination functions.

Although numerous improvements have been made over the years, the fundamental aspects of vitreous cutters are known and taught by O'Malley and Heintz in U.S. Pat. Nos. 3,815,604 and 3,884,238, respectively. In its modern form, the axial guillotine cutter is relatively small, lightweight, durable, cheap, and exhibits excellent cutting characteristics.

One negative aspect of guillotine cutters, whether pneumatically or electrically operated, axial or rotary, is that the flow through the cutting port is discontinuous, being interrupted when the cutting blade passes across the port. In vitreous surgery, this can often be observed as "vitreous bounce," as the vitreous is alternately pulled into the port and released. This, in turn, can make removal of vitreous close to the retina hazardous, as the retina may become detached or may be inadvertently drawn into the cutting port.

Sussman and Zaleski, for example, provide one solution to this problem in U.S. Pat. No. 5,284,472. An alternative solution, however, is to increase the cutting rate. It is observed in clinical practice that the vitreous bounce is reduced to a negligible level when the cutting rate is high, generally in the range of 1200 to 1500 cuts per minute (cpm) or more. In U.S. Pat. No. 5,176,628, for example, Charles et al. state that increased cutting rate (up to 1200 cpm) is a desirable cutter characteristic.

Various improvements have gradually raised the maximum cutting rate of pneumatic axial guillotine cutters from 420 cpm in the 1970s to 600 cpm in 1982 and to 800 cpm in 1992. In contrast, high-speed cutting has been available from the very earliest electrically-operated guillotine cutters. Peyman and Dodich claim operation of an electric cutter at 3000 cpm in U.S. Pat. No. 3,776,238.

The principal reason for the slow progress with pneumatically-operated cutters is the physics of moving gas through a long interconnecting tube to drive the surgical handpiece. In order to preserve sterility in the vicinity of the patient and surgeon, the console containing the driver mechanism (which supplies the pneumatic energy to drive the cutter) is located at a considerable distance from the patient. The surgical handpiece is typically connected to the console through 72" to 84" of tubing. The rate at which the pneumatic pressure at the handpiece end of the tubing can change is limited by the physics of compressible-gas flow. In particular, the flow velocity through the tube cannot exceed the speed of sound.

Eight hundred cpm is not the ultimate speed limit for pneumatic axial guillotine cutters. A speed of 1500 cpm has been successfully demonstrated in a cutter positioned at the end of 84" of tubing. To achieve this performance, however, requires coordinated improvements in both the surgical handpiece and the pneumatic driver mechanism in order to overcome the physical limitations of the intervening tubing.

While a high cutting rate is desirable for removing vitreous close to the retina, a high cutting rate is not desirable for removing material at other locations in the eye. The rate of removal of vitreous is significantly greater at a cut rate of 500 to 600 cpm than it is at a cut rate of 1500 cpm. This is because the vitreous is removed in "nibbles" at 1500 cpm and in "bites" at 600 cpm. Thus, when vitreous bounce is not a concern, such as when removing material at the center of the eye, it is desirable to remove vitreous at a lower cut rate.

Despite the known benefits of having an adjustable-speed, pneumatic cutter that is also capable of operating at high speeds, few if any cutters exist that offer such functionality. Since high-speed choices are limited, some surgeons have resorted to using modern electrically driven probes even though they are expensive, heavy, and have a tendency to vibrate excessively.

SUMMARY OF THE INVENTION

Accordingly, there is a need for a vitreous cutter that can provide a high cutting rate, but retain as much as possible the advantages of the present pneumatically-operated vitreous cutters in terms of size, shape, weight, vibration, torque, low or minimal heat generation, and low cost.

In general terms, the invention provides a system having a pneumatically-operated axial guillotine cutter and a pneumatic driver mechanism that is capable of high-speed operation (at least 1200 cpm) with 84" of intervening tubing. The pneumatic driver module or subsystem of the invention is suitable for incorporation into a vitreoretinal surgical system so as to provide a high-speed cutting function when used with an appropriate surgical handpiece. The invention also provides a pneumatic driver module suitable for attachment to an existing vitreoretinal surgical system so as to provide a high-speed cutting function when used with an appropriate surgical handpiece. The invention also provides a pneumatic driver module with a human interface for conveniently selecting one of two operating modes: a lower cutting rate for rapid removal of vitreous in the center part of the eye (a "cut" mode), and a higher cutting rate for more controlled removal of vitreous near the retina (a "shave" mode).

As noted, one embodiment of the invention is a subsystem or module to be incorporated into a surgical system. A very desirable alternative embodiment, however, is a free-standing module that could be purchased and attached to an existing vitreoretinal surgical system so as to upgrade the cutting rate without the necessity of replacing the entire surgical system in order to obtain this feature.

The present invention includes a system with a high-speed pneumatically-driven vitreous cutter, capable of operating at a cutting rate above 800 cpm, the maximum currently achievable with standard probes. In at least one embodiment, the cutter can operate at even higher speeds (above 1000 cpm), so that it can shave tissue. Because it has such capabilities, the cutter is referred to as a "cut and shave" or "C & S" probe. In addition to high-speed functionality, the cutter or C & S probe can also be operated at peak pressure as low as thirteen (13) pounds per square inch (psi), an efficiency not previously achieved. Prior systems operated at pressures of about 20 to 30 psi.

The system includes a driver or actuator that powers the cutter. The actuator provides pressure pulses that can drive the cutter at cutting rates above 800 cuts per minute. The actuator is capable of supplying the appropriate pulses through an actuation or connection tubing of about 72" to about 84" in length. The actuator produces pulse trains at a frequency selectable by the user.

The invention may be implemented in one of two general forms. In the first form, the invention is implemented as a stand-alone or individual unit separates from a vitrectomy machine, phaco emulsification machine, or combined vitrectomy/phaco emulsification machine (generally referred to as a "surgical machine"). The inventors have developed at least two actuators that can take this form.

The first stand-alone actuator is designed to be attached to a surgical machine, such as a machine designed to operate a known 30 psi probe at a cut rate (frequency) of at least 600 cpm. The actuator of the present invention develops the pneumatic energy needed to operate a cutter at high speed by capturing the pneumatic output of the surgical machine. A waveform shaping circuit then controls a valve that converts the captured pneumatic energy into pulse wave trains to actuate the cutter (or C & S probe) at high frequencies. The actuator includes a human interface, which has input keys to allow a user to select the operating frequency of the cutter and a display to indicate the selected frequency and other conditions in the system.

The second stand-alone actuator is designed to be attached to a surgical machine that does not produce sufficient pneumatic energy to drive a cutter at high speeds. The second actuator develops its pneumatic energy using a pneumatic module having a small (typically less than 150 cubic inch or 2.5 liter), lightweight (less than 2 Kg), and low-noise compressor unit. A compressor control circuit drives the compressor motor only as hard as is required to produce pulse trains at the user-selected frequency.

One additional feature of both of the stand-alone embodiments is that the cutter on/off signal comes from the surgical machine. A further benefit of the stand-alone actuators is that no modifications or variations in the host surgical machine are required to operate the actuators.

The second method of utilizing the teachings of the present invention involves integrating an actuator module into a surgical machine. At least two types of actuators can be implemented in an integrated form. The first integrated embodiment is designed to be integrated into a surgical machine that uses an external pressure source. The external pressure source is then coupled to a pressure regulator within the actuator. The pneumatic energy appropriate for a high-speed cutter can be obtained through the regulator. A waveform shaping circuit is used to generate the pressure wave appropriate to actuate the cutter.

In the second integrated embodiment, the actuator in the surgical machine includes a small compressor. Thus, this embodiment does not require an external pneumatic power source. The cutting rate controls and the interface for adjusting the rate of cutting and displaying operational conditions of the surgical machine is modified to permit the display of the extended cutting frequency range of the cutter of the present invention. Like the other embodiments, a waveform shaping circuit is used to control the output valve to generate pulse trains used by the cutter.

No matter what form is used, each of the actuator embodiments contemplated may be used with a single, small, lightweight, pneumatic cutter or C & S probe.

As is apparent from the above, it is an advantage of the invention to provide an improved surgical cutter. Other features and advantages of the invention will be apparent by consideration of the detailed description and drawings.

BRIEF DESCRIPTION OF THE DRAWINGS

In the drawings:

FIG. 1 is a block diagram of a high-speed cutting system made in accordance with the teachings of the present invention.

FIG. 2 is a simplified, cross-sectional view of a cutter used in the present invention.

FIG. 3 is a block diagram of an actuator constructed in accordance with the teachings of the present invention.

FIG. 4 is a schematic diagram of one embodiment of an actuator suitable for use in the present invention.

FIG. 7 is a schematic diagram of a second embodiment of an actuator suitable for use in the present invention.

FIGS. 7A–7C are circuit diagrams of an exemplary compressor control circuit constructed in accordance with the teachings of the present invention.

DETAILED DESCRIPTION

Figure 5:
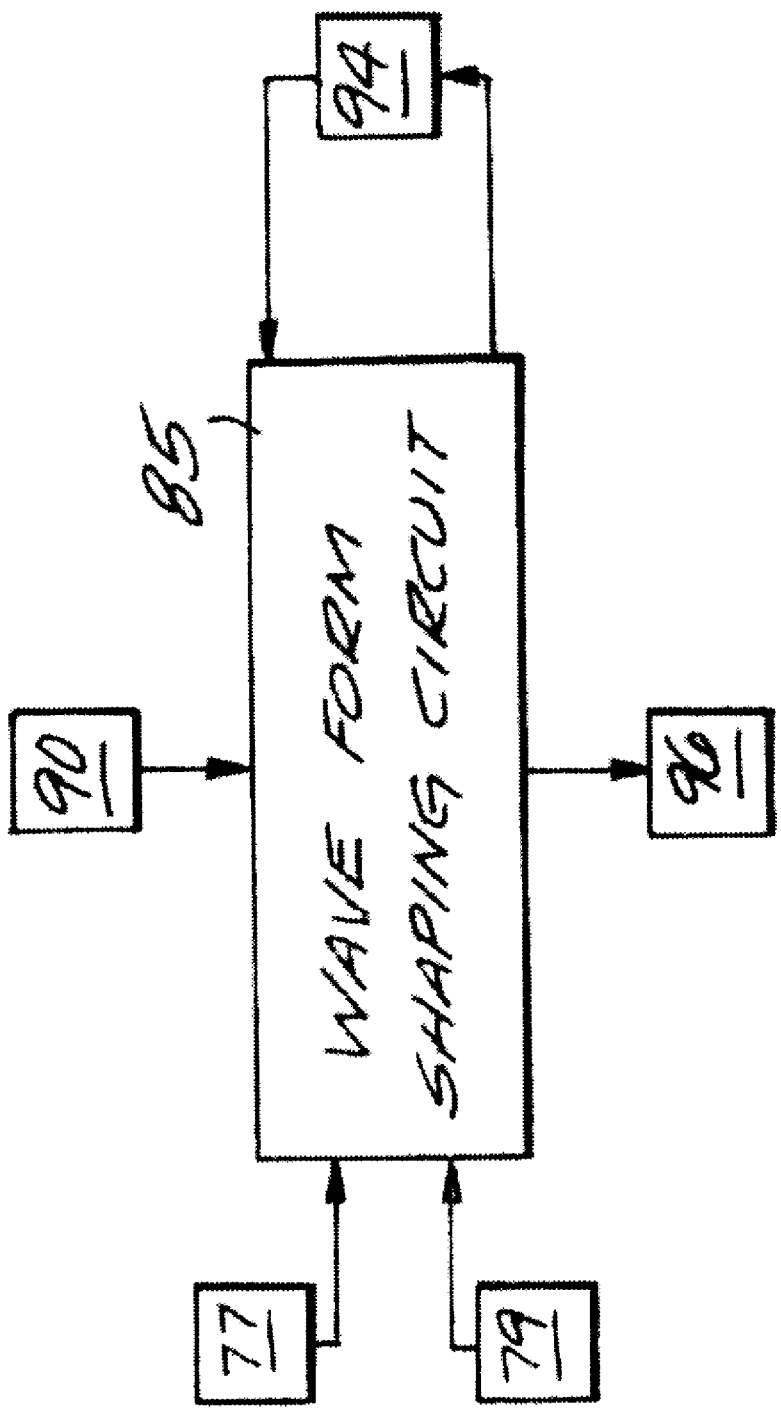
FIG. 5 is a schematic diagram of the waveform shaping circuit used in the present invention.

A generic high-speed vitreous cutting system 10 is shown FIG. 1. The system 10 includes an actuator 12 and a cutter 14 connected to the actuator through a tubing 16. The cutter is also connected through a tubing 18 to an aspiration system, which is separate from the vitreous cutting system 10. Preferably, the tubings 16 and 18 are joined as a single, twin-bore tubing. Typically, the tubing is 72" to 84" in length.

As best seen by reference to FIG. 2, the cutter 14 is a pneumatically driven, axial guillotine-type vitreous probe or cutter. The cutter has a generally cylindrically-shaped housing 19 designed to be held in a human hand and may be approximately 1.5" in length. The housing 19 has a front end 20 and a rear end 22. The rear end 22 has a connector 23, designed to receive one end of the tubing 16, and a center opening 24. Inside the housing 19 is a flexible diaphragm/piston 25 having a first side 26 and a second side 27. The first side 26 and rear end 22 define a rear chamber 30. The piston 25 is connected to an inner cutting tubing 32. The tubing 32 is inserted through the center opening 24, axially movable in a linear fashion in two directions A1 and A2, and in communication with the aspiration tubing 18, either by direct connection or through a coupling means (not shown) incorporated into rear end 22 of the housing 19. An O-ring or similar device 34 seals the interface between the tubing 32 and opening 24. The piston 25 is biased in a first position P1 by a biasing mechanism 36, such as a spring. The biasing mechanism 36 is positioned between the second side 27 of the piston 25 and the first end 20 of the housing 19.

The first end 20 of the housing 19 has a tube opening 39. An O-ring or similar device 42 seals the interface between the inner cutter tubing 32 and opening 39. An outer cutter tubing 40 is inserted in the opening 39 and extends outwardly from the first end 20 of the housing 19. Preferably, the tubing 40 extends approximately 1.2 to 1.4 inches from the first end 20. The outer cutting tubing 40 is coaxial with the housing 19. The outer cutting tubing 40 has a distal end 44 with a cutting port 45.

When the cutter 14 is in use, negative pressure is conducted through the aspiration tubing 18 and inner cutter tubing 32 and delivered to the cutting port 45 to aspirate soft material from the surgical site. An actuating pulse is delivered through the actuation tubing 16 into the chamber 30. This causes the diaphragm 25 to push against the biasing mechanism 36 and move in the direction A2. Movement of the diaphragm causes the inner cutting tubing 32 to move across the cutting port 45 and cut material that is situated in the port 45. At the end of the actuating pulse or when the actuation pressure is reduced, the biasing mechanism 36 moves the diaphragm back to the position P1. Therefore, an actuation pulse train will cause the inner cutter tubing 32 to move in the linear directions A1 and A2 cyclically.

The friction between the cutter tubing 32 and the outer tubing 40 affects the efficiency of the cutter 14. However, a close fit between the cutter tubing 32 and the outer tubing 40 is required in the vicinity of the cutting port 45 in order to effectively cut the material aspirated into the port. A close fit with low friction is achieved by using an inner tubing 32 with an outer radius substantially less than the inner radius of the outer tubing 40, by circularly flaring the distal end of inner tubing 32 to an outer radius which approximates the inner radius of the outer tubing 40, and by bending the inner tubing 32 so as to resiliently bias the distal end of inner tubing 32 against the inner surface of the outer tubing 40 along the side wherein the cutting port 45 is disposed. The inner tubing 32 has a thinner wall (2 to 3 mils) than is conventional for other vitreous cutters in order to give greater resilience. Alternatively, the resilient bias could be produced by bending the outer tubing 40 so that the cutting port 45 is displaced toward the inner tubing 32.

Improving the efficiency of the cutter permits it to be operated with low-pressure pulse trains. With the present invention, the cutter 14 may be operated at peak pressure of thirteen (13) psi. This is of particular significance because 13 psi is the critical pressure for air or nitrogen at sea-level conditions. At the critical pressure, the flow through a restriction, such as the tubing 16, reaches the velocity of sound. Operation at pressures higher than this is particularly inefficient, because the velocity cannot increase despite the additional pressure. The improved efficiency of the cutter 14 has the additional benefit of improved efficiency in delivering pneumatic energy through the interconnecting tubing 16.

The actuator 12 is shown schematically in FIG. 3. In the general form shown, it consists of two sections; a pneumatic energy generation section 50 and a pulse train control section 52. As noted above, the present invention may take multiple forms depending on the implementation of the actuator. Each of the forms is described below.

An actuator 55 made in accordance with one embodiment of the present invention is shown in FIG. 4. The actuator 55 has a pneumatic energy generation section 57 and pulse train control section 59 contained within a housing 60. The actuator 55 is designed to convert the pneumatic output pulses from a surgical machine (not shown) to a pressure pulse train which may have a frequency of 1500 cpm or more.

Output pulses from the surgical machine are delivered to the actuator 55 through an input tubing 62. The input tubing 62 has an input connector 64, such as a female luer lock or a quick connect/disconnect connector that mates with the output port (not shown) of the surgical machine. A check valve 66 is placed in the tubing 62 to prevent the flow of fluid or pulses back to the surgical machine. The input tubing 62 is terminated by a connector 68 which mates with a fitting 70 located in the enclosure 60.

Pressurized fluid directed to the actuator 55 travels from the input tubing 62 to a pressure regulator 72 (which is used to adjust and limit the pressure level output to downstream devices). The pressurized fluid is then directed through a connecting tubing 74 to an accumulator 75, where pneumatic energy is captured. Although shown as a separate, cylindrical component, the accumulation of energy may be accomplished in tubing or similar items that connect the components of the system. Thus, in the present invention, the term accumulator is not to be limited to the example illustrated.

Pressure from the accumulator 75 is delivered to a solenoid valve (discussed below) through a tube 76. The pressure level before the regulator 72 is monitored by a first pressure transducer 77. The pressure in the accumulator 75 is monitored by a second pressure transducer 79. The output signals from the two pressure transducers are delivered through lines 81 and 83 to a waveform shaping circuit 85 in the pulse train control section 59. The waveform shaping circuit 85 is powered by a power supply 90 fed by an external power input line 92. The power supply 90 also supplies electrical power to a control and display unit 94. The waveform shaping circuit 85 and control and display unit 94 will now be discussed in detail.

As best seen by reference to FIG. 5, the waveform shaping circuit 85 receives the frequency and other commands (such as power on/power off) from the control and display unit 94. It also receives signals from the pressure transducers 77 and 79. Based on the input data, the circuit 85 then generates an output command signal which is delivered to a solenoid valve 96 so that the pneumatic output waveform from the valve 96 will be the appropriate waveform to activate the cutter 14 for vitreoretinal surgery. Preferably, the solenoid valve is a "three-way" valve. That is, the valve has a common port (in communication with the cutter) that is connected to pressure when the valve is energized and is vented otherwise.

The output command signal delivered to the solenoid valve 96 is a sequence of square waves. The command signal is of such a form as to compensate for the parameters controlling the pressure waveform at the cutter end of the tubing 16. These parameters include the pressure in and the volume of the accumulator; the aperture size of the valve (both of the output port and the exhaust port); the pulse rate of the valve driving signal; the speed of the valve response; and the length, inner diameter, durometer, and flow resistance of the tubing and connectors. It should be noted that the present state of the art permits proper choice of most of the parameters so that, with a fixed pulse width, a relatively consistent pressure waveform can be produced to drive a 20 to 30 psi cutter up to about 800 cuts per minute (cpm). The inventors have found that a fixed pulse width pressure waveform is unsuitable to drive a cutter at frequencies above 800 cpm. One reason for this appears to be that since the cycle time is shortened, there is not enough time to allow the pressure to exhaust to zero in a cycle. The residual pressure causes subsequent pulses in the pulse train to have an increased peak pressure (until balanced at both a higher peak pressure and a higher minimum pressure as the cutting frequency increases). This decreases the cutting port opening time, which in turn, prevents the cutter from returning to its fully open position. In this state, the cutter does not aspirate effectively. Another reason present technology is unsuitable for driving a cutter above 800 cpm, is that the pressure level in the accumulator decreases as the cutting rate increases due to increased output flow. This causes peak pressure to decrease proportionally.

In contrast, in the present invention pulse width is changed when high cutting rates are desired or the accumulator pressure changes. The change is such as to maintain the peak pressure delivered to the cutter at the end of the interconnecting tubing at an approximately constant level. This helps reduce residual pressure, which in the present invention may be kept below about 2 psi (see FIG. 5B). The wave shaping circuit 85 controls the pulse width of the valve-driving signal (pressure waveform) as both a function of the operating pulse frequency and the real-time source pressure. Specifically, the waveform shaping circuit controls the pulse width according to the following equation:

$$T(P_s, F) = T_{800} - \alpha \cdot \ln[(P_s - \gamma)/(P_{s0} - \gamma)] - \beta(F) \cdot [F - F_{800}] \quad \text{(Eqn. 1)}$$

where

T is the pulse width, $P_s$ is the source pressure or pressure in the accumulator, F is cutting frequency, α is a coefficient specific to the system design, γ is a constant specific to the system design, and β(F) is a frequency dependent coefficient specific to the system design.

As it is created, the pressure wave output (or pulse train) of the valve 96 is conducted through tubing 98 to an output fitting 99, such as a male luer lock fitting. When the system is in use, the pressure wave output is delivered to the cutter 14, which is coupled to the output fitting 99 through the tubing 16.

As best seen by reference to FIG. SA, the waveform shaping circuit 85 may be implemented using operational amplifiers, comparators, and discrete circuit components. Of course, the control functions carried out by the waveform shaping circuit may be implemented using microprocessors and other programmable devices. As embodied in FIG. 5A, the waveform shaping circuit 85 includes an input section 100. The input section 100 receives the cutting rate selected by the user (as described below) and outputs a pulse train corresponding to the selected rate to node N1. The output from the input section 100 is "OR'ed" at node N2 with the amplified output from pressure transducer 77 delivered at pin 14 of integrated circuit U2. The pulse train from the input section 100 is delivered to the pulse modification section 102 when the pressure transducer 77 detects activity by the surgical machine (not shown). The pulse modification section 102 sets the duration of the pulse (i.e., the time that the valve 96 is open or turned on) according to the frequency rate set by the user and adjusts that pulse duration according to the pressure available in the accumulator as measured by the second pressure transducer 79.

Preferably, the pulse modification section 102 maintains the pulse width at a constant amount (e.g., about 18 ms) for cut rates less than a predetermined amount; for example, about 800–1000 cpm. For cut rates above the predetermined level, the pulse width is reduced. As embodied in the examples shown herein, at the maximum cut rate the pulse width is reduced to about 15 ms.

The preferred response of the pulse modification circuit 102 to the real-time accumulator pressure measured by transducer 79 is according to the logarithmic function of Equation 1. This relationship has been shown empirically to give good results over a wide range of operating conditions, including operation at high altitude. Over a narrower range of operating conditions, of course, a linear approximation may give adequate results.

The pulse modification circuit 102 is implemented as a cascade of two timing circuits, the first of which (with output at pin 13 of integrated circuit U4) is responsive to the pressure transducer 79 and the second of which (with output at pin 14 of integrated circuit U4) is responsive to the pulse rate of the pulse train delivered from the input section 100. The duration of the pulse delivered to the valve 96 (at connector J2) is the sum of these two time intervals. In the embodiment shown, the pulse width can be adjusted by offsetting the pressure transducer signal by means of potentiometer R20. In an alternate embodiment, not shown, a third timing circuit is included in the cascade which has an adjustable element, so that an unmodified pressure transducer signal is available for other purposes.

Figure 5A:
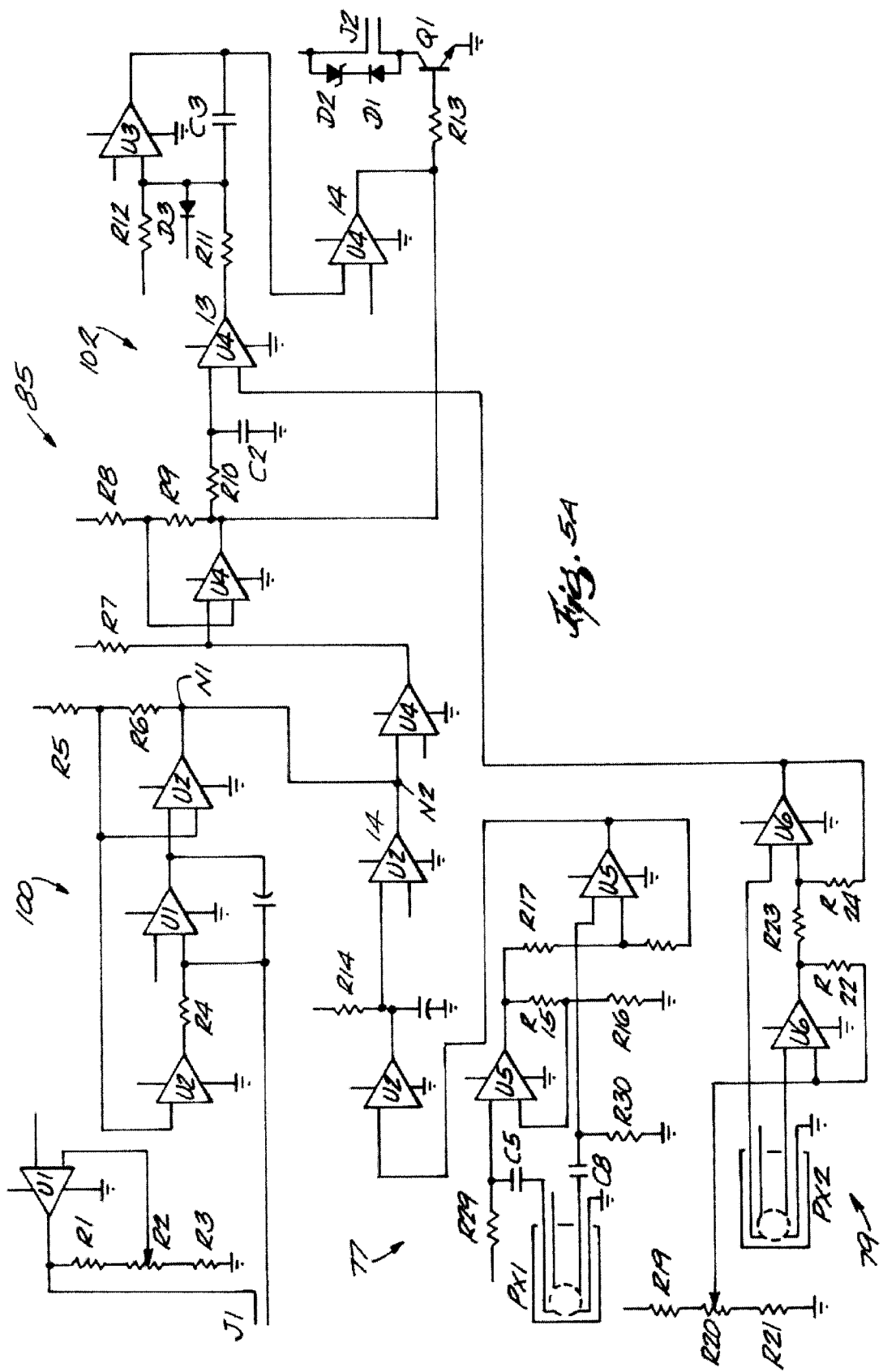
FIG. 5A is a circuit diagram of an exemplary waveform shaping circuit constructed according to the teachings of the present invention.
Figure 5B:
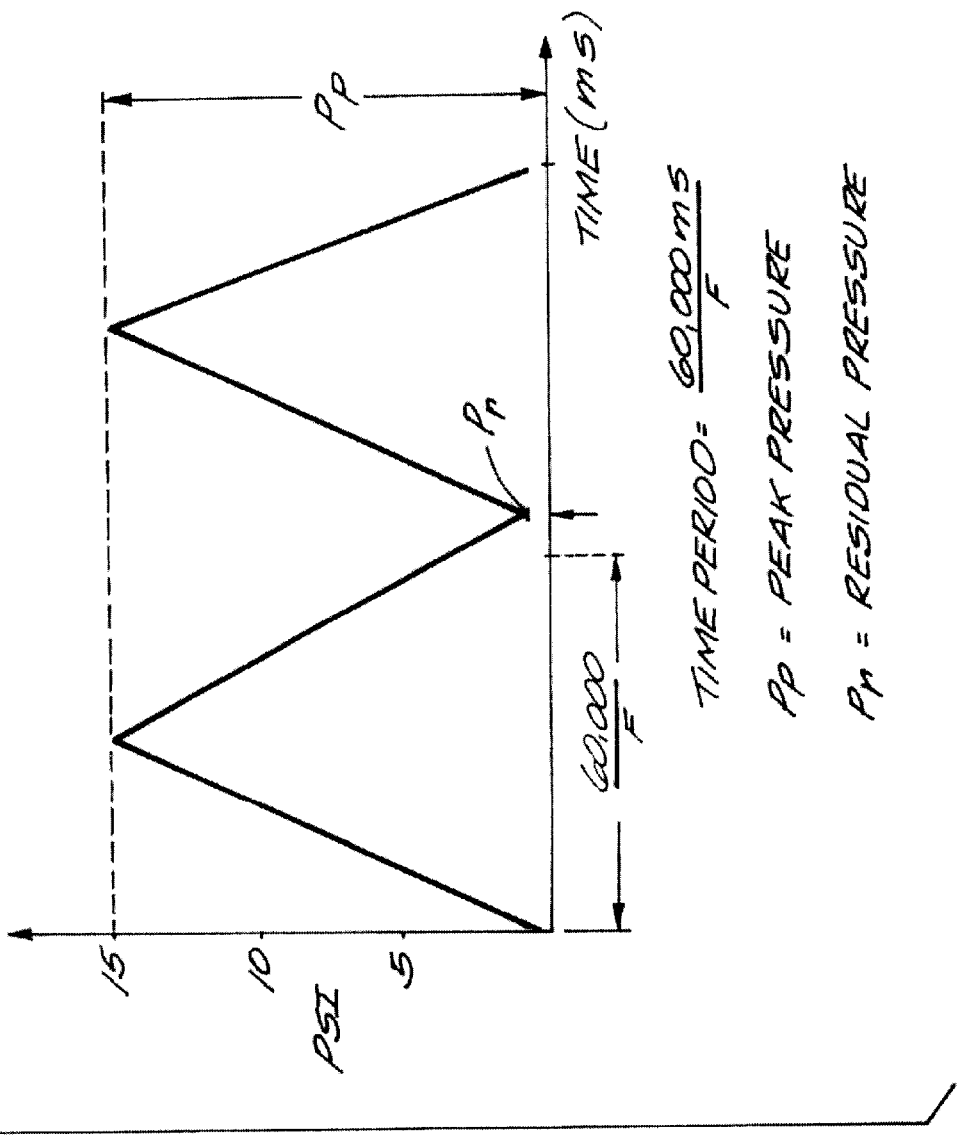
FIG. 5B is a waveform diagram illustrating an exemplary waveform delivered to a cutter used in the present invention.
Figure 5C:
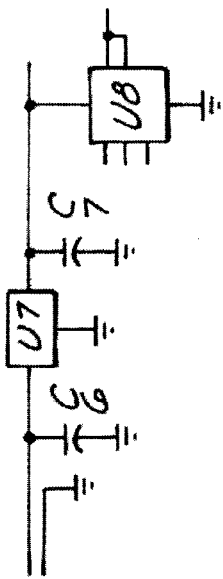
FIGS. 5C–5E illustrate power supply circuits used with the waveform shaping circuit shown in FIG. 5A.
Figure 5D:
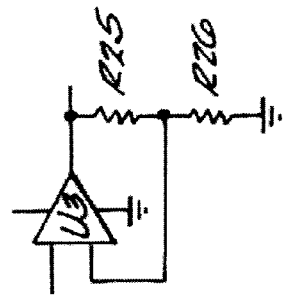
Figure 5E:
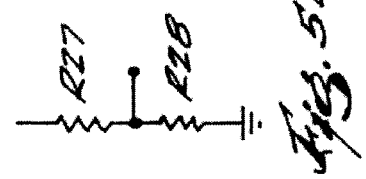

As noted, the waveform shaping circuit 85 is powered by the power supply 90. When the waveform shaping circuit 85 is implemented as shown in FIG. 5A, the power supply provides three different voltages using the circuits illustrated in FIGS. 5C–5E.

Figure 6:
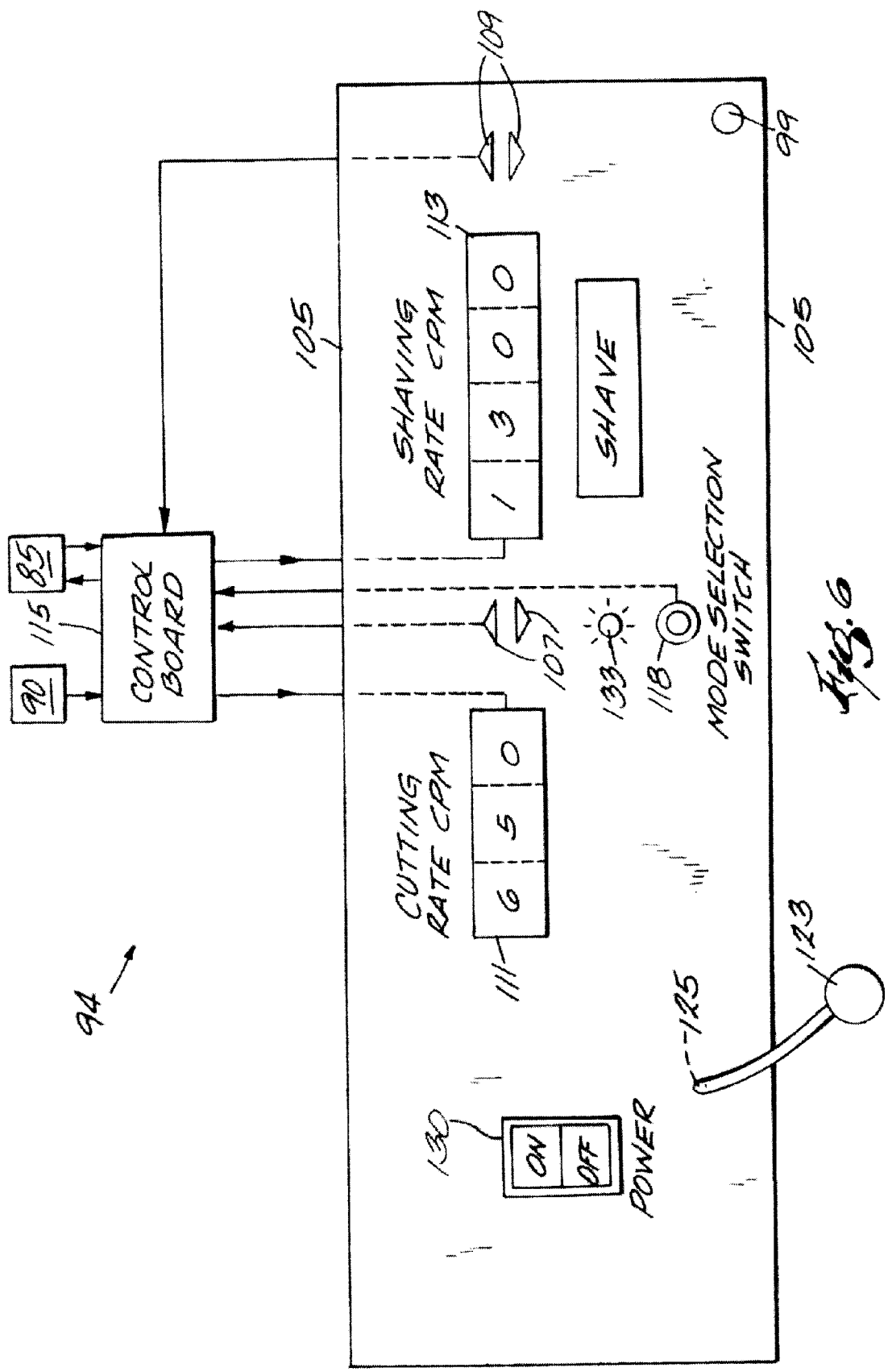
FIG. 6 is a schematic representation of a user interface of the actuator shown in FIG. 4.
Figure 13:
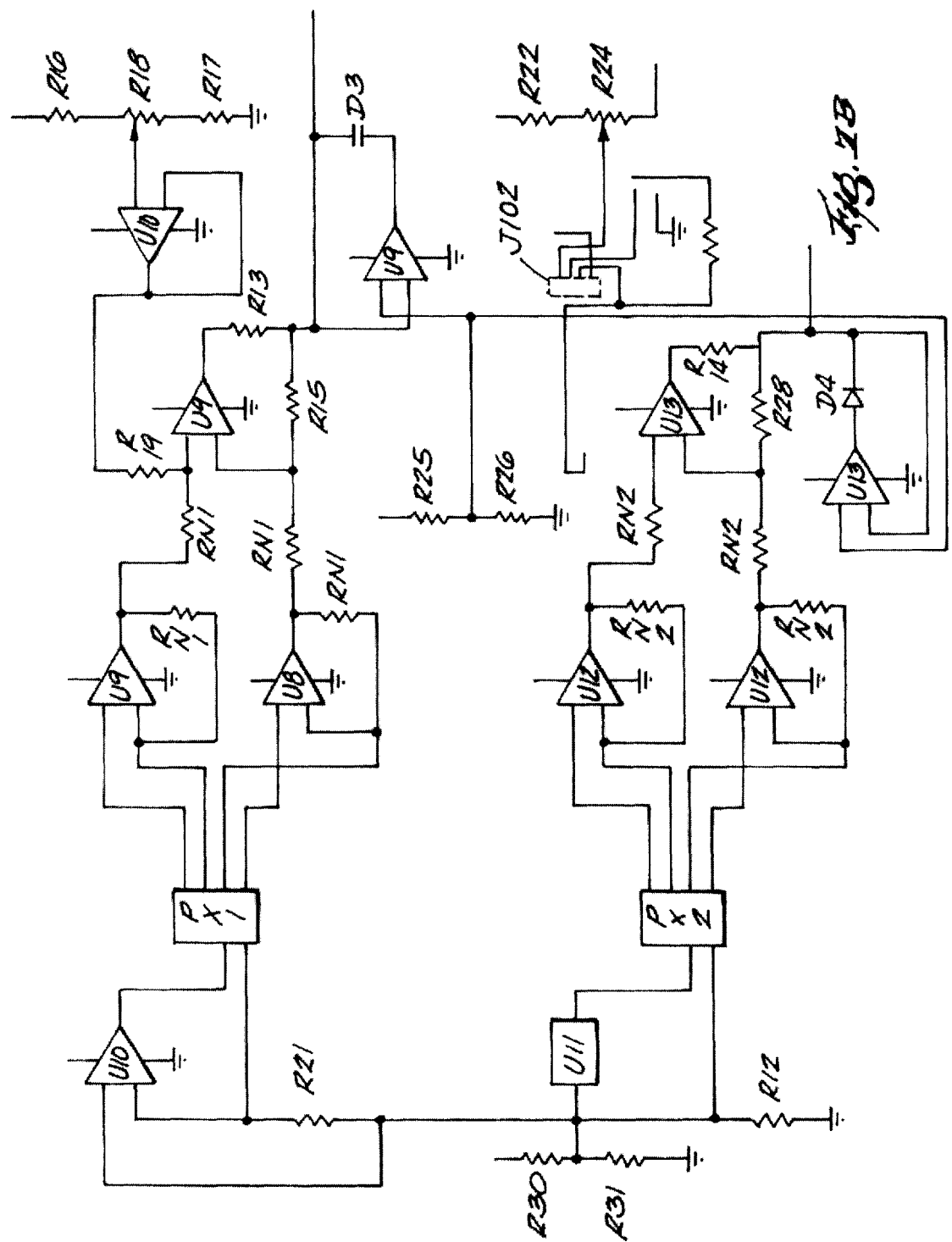

The control and display unit 94 is shown in greater detail in FIG. 6. Preferably, the control and display unit 94 includes a front panel 105 with two independent frequency selection controls 107 and 109 and two corresponding digital frequency displays 111 and 113, as shown. The control and display unit 94 includes a control board 115 powered by the power supply 90. The control board 115 generates an electronic signal to provide the frequency information to the waveform shaping circuit 85. The frequency information is input into the actuator through the switches 107 and 109 and a mode switch 118. The mode switch 118 allows a user to control the system in a "cut" or a "shave" mode and, in the embodiment shown, the switch 118 is set up so that each press of the switch 118 causes a change in mode (i.e., a change from "cut" to "shave" or "shave" to "cut"). The frequency output to the cutter corresponds to either the "cutting rate" (typically 60 to 800 cpm) selected using the switches 107 (if the "cut" mode was designated with the switch 118) or the "shaving rate" (typically 800 cpm and higher) selected using the switches 109 (if the "shave" mode was selected with the switch 118).

Alternatively, the selection of the mode can be accomplished using a remote switch 123, instead of the switch 118. If used, it is preferred that the switch 123 be an autoclavable momentary switch placed in the instrument tray in the sterile field or a footswitch placed under the surgical table. Both of these types of switches can be easily controlled by the operating surgeon or an assistant during a surgical procedure. In FIG. 6, the remote switch 123 is shown hard-wired to the front panel 105 through a connecting socket 125. Alternatively, the remote switch 123 may be coupled in data communication through a wireless transmission system or connected to the control board through a plug or socket in the side or back of the actuator 55.

In order to indicate the mode of operation, only one of the digital frequency displays 111 and 113 is highlighted to indicate the frequency chosen for cutter actuation. Selection of the cutting and shaving rates is usually done prior to the surgical procedure, but the present invention permits the user to change the rate during operation too. The rate is changed by simply inputting the desired frequency using the switches 107 and 109. Of course, it should be understood that while described as pushbuttons and switches, the input devices on the control panel 115 may be levers, knobs, dials, sensors, or other suitable input mechanisms.

The front panel 105 also includes a power switch 130 that controls the power source 90. The power switch 130 can be located on the front of the panel 105 as show in FIG. 6 or any other convenient location. The panel 105 may include an illuminator 133, such as an LED, to indicate the power on/power off condition.

Another embodiment of the present invention, actuator 150, is shown in FIG. 7. The actuator 150 shares many features with the actuator 55, such as a pneumatic energy generation section 153 and pulse train control section 155. Further, the actuator 150 may be constructed with the accumulator 75, waveform shaping circuit 85, control and display unit 94, solenoid valve 96, and output fitting 99. However, unlike the actuator 55, the actuator 150 includes a source of pressurized air, such as a compressor 157. Preferably, the compressor 157 is a small (typically less than 150 cubic inch or 2.5 liter), lightweight, low-noise compressor. The compressor 157 is controlled by a control circuit 160 which drives the compressor motor only as hard as needed to produce sufficient energy required for the real time usage at the actuation frequency selected.

The actuator 150 is designed to be used in combination with a surgical machine 165, such as a vitrectomy machine, phaco emulsification machine, or combination vitrectomy/phaco emulsification machine. A hose 166 is connected to the cutter driving port (not shown) of the surgical machine 165 and to the pressure transducer 77. The pressure transducer 77 sends an on/off command to the waveform shaping circuit 85 that corresponds to the activity of the surgical machine 165. Thus, as the surgical machine outputs a pneumatic signal, the actuator 150 is activated. The actuator 150 may also be provided with a direct electrical connection 167 to the wave-form shaping circuit 85 for use with the surgical machine 165, should it have an electrical, rather than pneumatic output.

The control circuit 160 sends a compressor control signal to the compressor 157 through a connection 168 to regulate the compressor so that it will generate only as much pneumatic energy as is required for operation of the cutter. The control circuit 160 monitors the pressure in the accumulator 75 using the input from the pressure transducer 79 and compares that pressure to a predetermined pressure $P_o$ and supplies energy to the motor at a rate that is proportional to the difference between the predetermined pressure $P_o$ and the measured pressure. In this way, the control circuit 160 extends the life of the compressor 157, and reduces the amount of heat and noise generated by it.

The control circuit 160 may be implemented as shown in FIGS. 7A–7B. It should be understood, however, that the control functions carried out by the control circuit 160 may be implemented using a microprocessor or other programmable device. Further, it may be possible to use a single microprocessor or programmable device to obtain the functions of both the waveform shaping circuit 85 and control circuit 160.

The waveform shaping circuit 85 receives pressure information from the pressure transducer 79, an actuation (or on/off) signal from pressure transducer 77 (as noted above), and actuation frequency commands from the control and display unit 94. In response to these inputs, the waveform shaping circuit 85 generates an output signal and sends it along data link 170 to control the solenoid valve 96. Like the previous embodiment, the valve 96 controls the pneumatic output of the accumulator 75. Pressure waves from the valve 96 are supplied to the actuation port 99. When the system is in use, a cutter, such as the cutter 14, is coupled to the actuation port 99. The actuator 150 is powered by the power supply 90.

Figure 8:
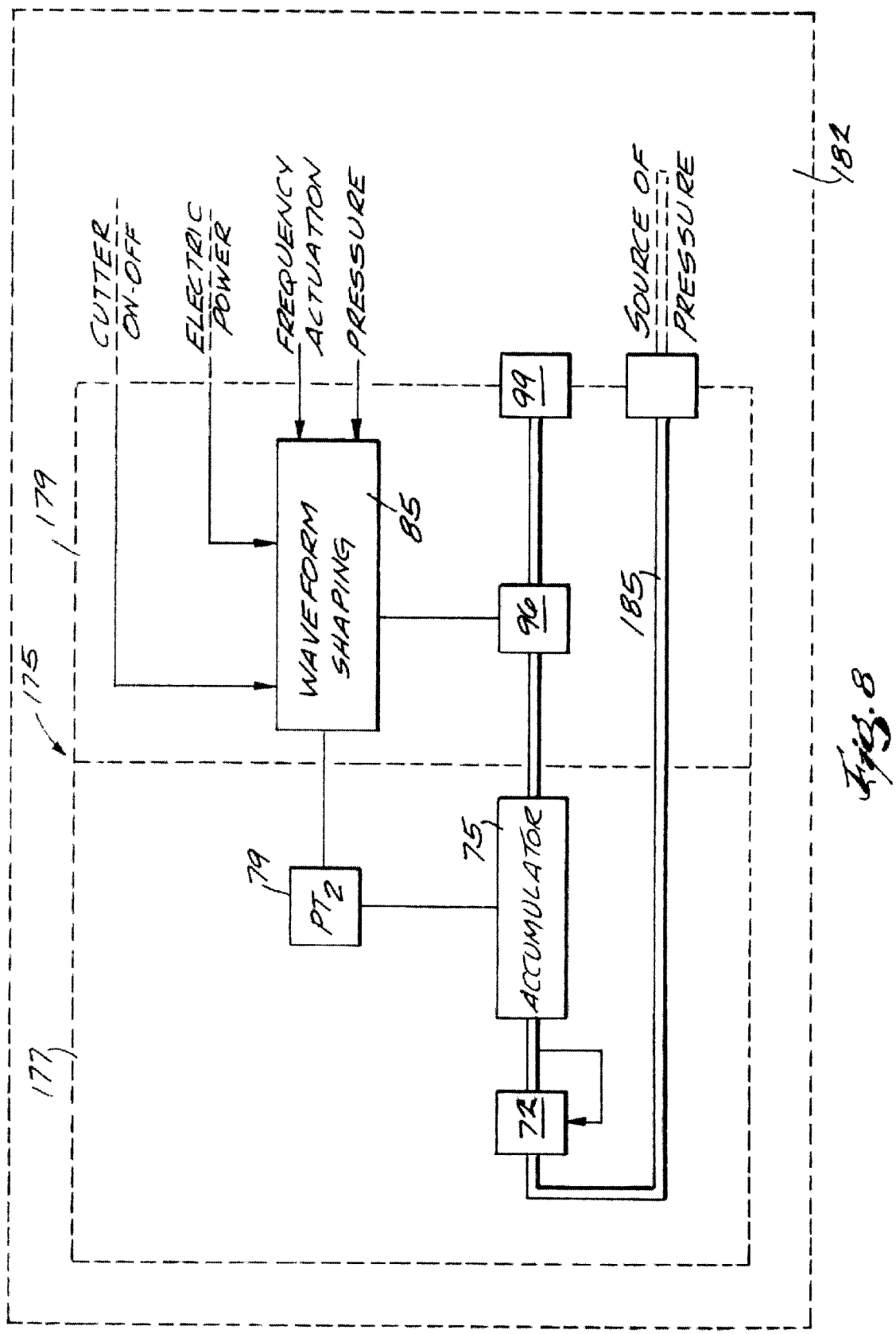
FIG. 8 is a schematic diagram of a third embodiment of an actuator suitable for use in the present invention.

FIG. 8 illustrates yet another embodiment of the present invention. In the embodiment shown, an actuator 175 having a pneumatic energy generation section 177 and a pulse train control section 179 is integrated into a surgical machine 182. The actuator 175 includes components common to the other embodiments discussed including the accumulator 75, waveform shaping circuit 85, solenoid valve 96, and output fitting 99. The actuator 175 operates with pneumatic energy received from the surgical machine 182. Specifically, pressurized fluid is received through a tube 185, regulated by the pressure regulator 72, and stored in the accumulator 75. The pressure level in the accumulator is monitored by the pressure transducer 79, the output of which is received by the waveform shaping circuit 85. Flow of pneumatic output from the accumulator 75 is controlled by the solenoid valve 96.

The waveform shaping circuit 85 receives power from the power supply for the surgical machine 182. The surgical machine 182 also supplies an on/off signal for the cutter, actuation frequency, and other pertinent information to the circuit 85. Based on this information and the pressure information from transducer 79, the circuit 85 generates a signal to control the solenoid valve 96. Pressure waves from the solenoid valve 96 are supplied to the output port 99 located on the surgical machine 182.

Figure 9:
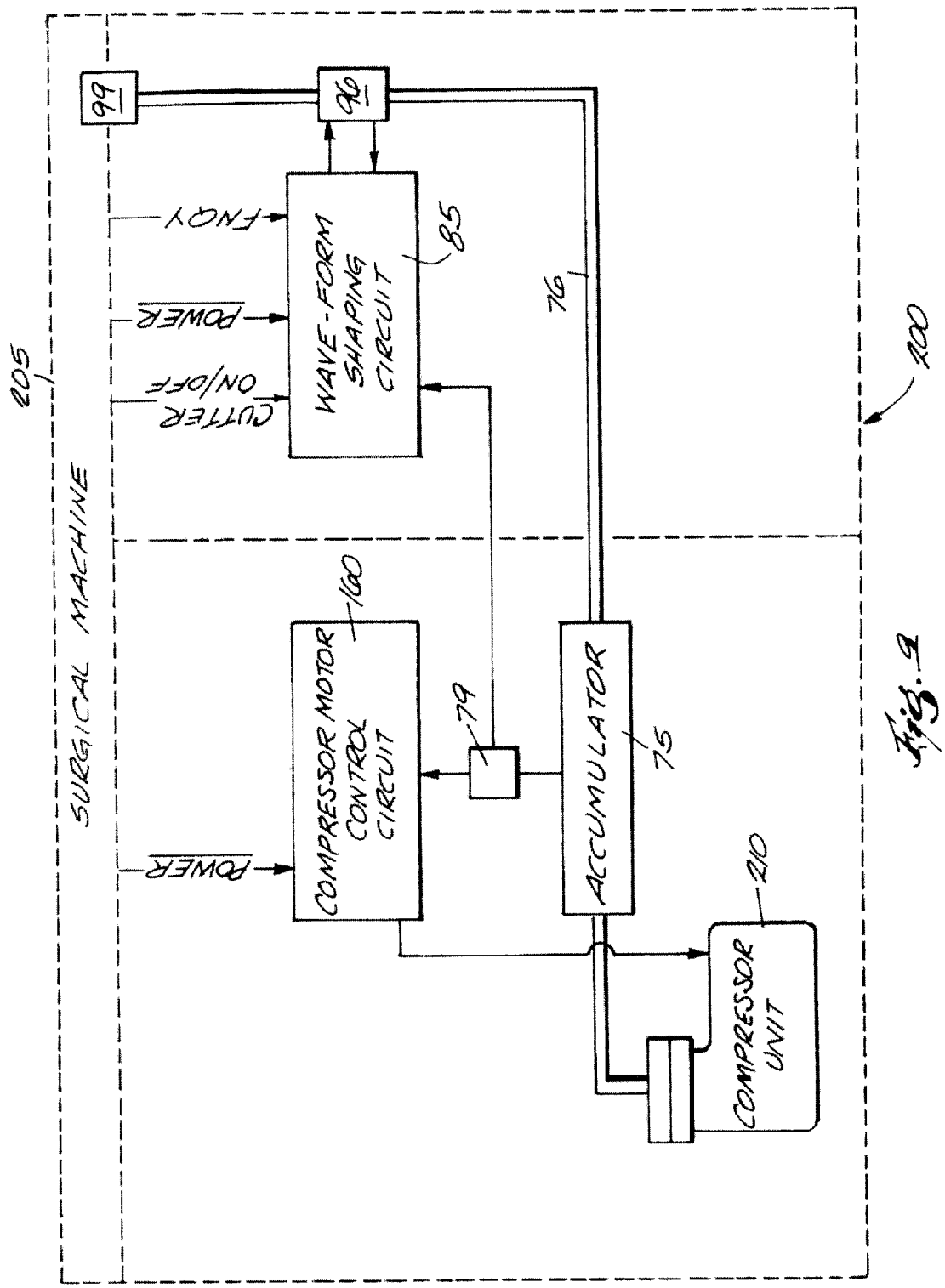
FIG. 9 is a schematic diagram of a fourth embodiment of an actuator suitable for use in the present invention.

Another embodiment of the present invention is shown in FIG. 9. An actuator 200 is incorporated into a surgical machine 205. In this embodiment, pneumatic energy is generated by a compressor 210. The compressor 210 may be the same as or similar to the compressor described above. The compressor 210 is controlled by the motor control circuit 160, which receives power from the surgical machine 205 and accumulator pressure information from pressure transducer 79. The pressure level of the accumulator 75 is also delivered to the waveform shaping circuit 85. The waveform shaping circuit 85 receives cutter frequency and cutter on/off commands from the surgical machine 205. Electrical power for components in the actuator 200 is supplied by the surgical device 205.

As in the other embodiments described, in the actuator 200 the waveform shaping circuit 85 generates a control signal to operate the solenoid valve 96 and the on-off or switching action of the solenoid valve 96 shapes or forms the pressure pulses delivered to the cutter 14.

Figure 10:
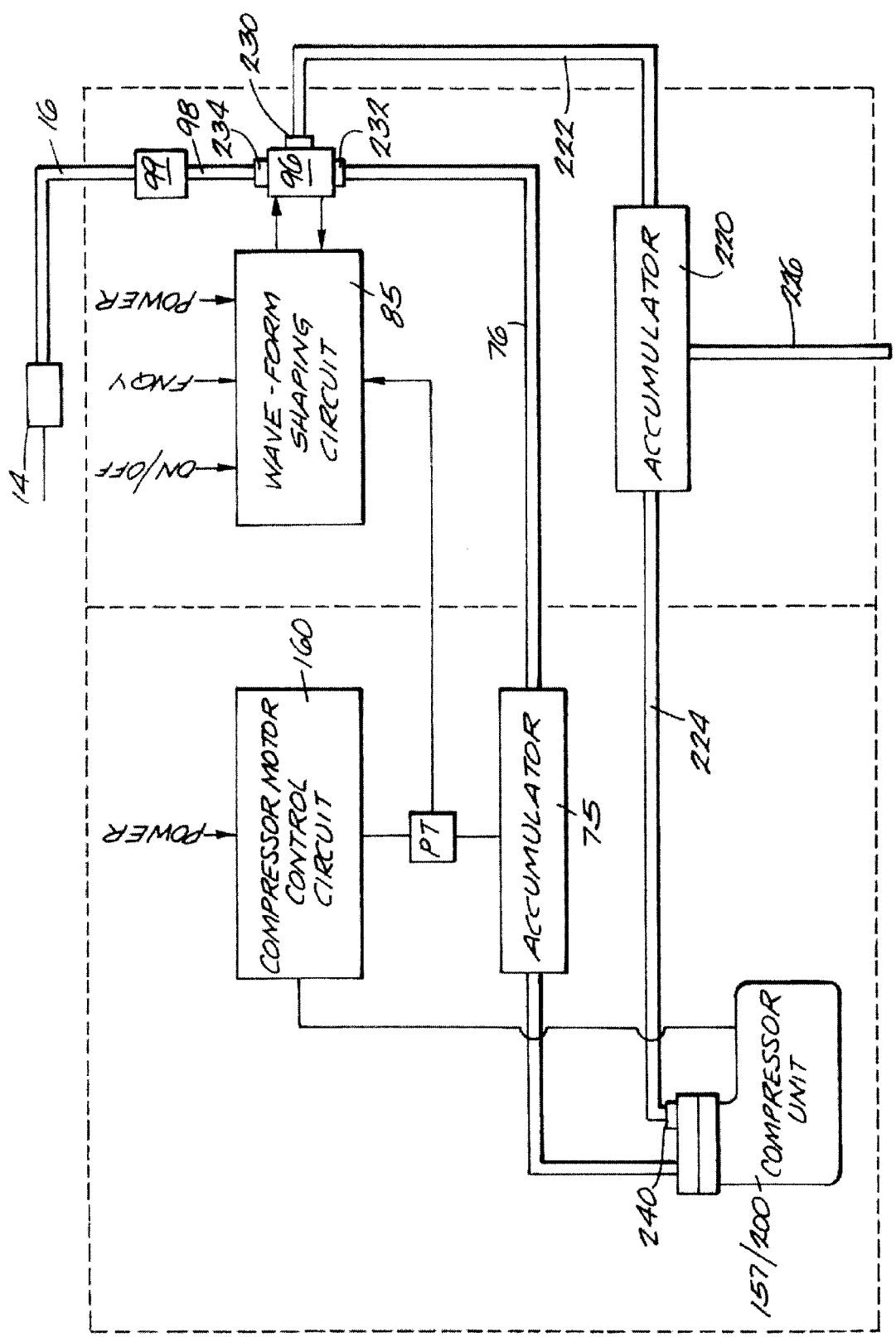
FIG. 10 is a schematic diagram of a fifth embodiment of actuator suitable for use in the present invention.

A further improvement, applicable to both the actuators 150 and 200, is shown in FIG. 10. For the actuators having a compressor unit, one of the principle objects of the compressor motor control circuit 160 is to reduce the operating noise of the compressor unit. Further noise reduction is possible by shielding from the environment the pulsating air flows at a valve exhaust port 230 and a compressor inlet port 240.

Conventionally, this is accomplished by means of mufflers or other sound-absorbing means connected between ports 230 and 240 and the atmosphere. These sound-absorbing means have a substantial resistance to air flow and therefore reduce the efficiency of the pneumatic system.

The inventors have found it useful to connect ports 230 and 240 together as a means of shielding them from the atmosphere. An accumulator 220 is connected between them by tubings 222 and 224 in order to maintain a more stable pressure at the valve exhaust port 230. Ideally, this arrangement could operate as a completely closed system, with the output of the compressor being delivered to the cutter 14 when the valve 96 is actuated to connect port 234 to port 232, and with the exhaust of the cutter 14 being returned to the input of the compressor when the valve 96 is actuated to connect port 230 to port 234. In practice, a connection 226 must be placed between the accumulator 220 and the atmosphere so as to compensate for leakage elsewhere in the system. This connection could include sound-absorbing means, but this has generally been found unnecessary.

Thus, the present invention provides an improved surgical cutter that operates with improved efficiency, at low pressure, and higher cutting speeds that previously achievable. Yet, the foregoing description describes only a few of the many forms that the present invention can take, and should, therefore, be taken as illustrative rather than limiting. It is only the following claims, including all equivalents that are intended to define the scope of the invention.

What is claimed is:

1. A pneumatic surgical cutting system comprising:
   a surgical machine operable to produce a first pneumatic output;
   an actuator coupled to the surgical machine, the actuator including:
      a first accumulator coupled to the surgical machine through a one-way valve to receive the first pneumatic output;
      a waveform control operable to control the width of a pressure pulse, coupled to the first accumulator, and activated when the surgical machine produces the first pneumatic output;
      a pressure regulator having an input and an output, the input being coupled to the first accumulator;
      a second accumulator coupled to the output of the pressure regulator; and
      a valve coupled to the second accumulator and the waveform control;
   a surgical cutter coupled to the valve by a tubing.

2. A system as in claim 1, wherein the valve outputs a pressure pulse train.

3. A system as in claim 2, wherein the pressure pulse train has a variable pulse width.

4. A system as in claim 3, wherein the waveform control controls the pulse width of the pressure pulse train as a function of a desired frequency.

5. A pneumatic surgical cutting system comprising:
   a surgical machine operable to produce a first pneumatic output;
   an actuator coupled to the surgical machine, the actuator including:
      a first accumulator coupled to the surgical machine through a one-way valve to receive the first pneumatic output;
      a waveform control coupled to the first accumulator and activated when the surgical machine produces the first pneumatic output;
      a pressure regulator having an input and an output, the input being coupled to the first accumulator;
      a second accumulator coupled to the output of the pressure regulator; and
      a valve coupled to the second accumulator and the waveform control, the valve outputting a pressure pulse train having a variable pulse width, and wherein the waveform control controls the pulse width of the pressure pulse train as a function of a desired frequency;
   a surgical cutter coupled to the actuator valve by a tubing; and
   a pressure sensor for sensing the pressure in the second accumulator.

6. A system as in claim 5, wherein the waveform control controls the pulse width of the pressure pulse train as a function of a desired frequency and the pressure of the second accumulator.

7. A pneumatic surgical cutting system comprising:
   a surgical machine operable to produce a first output;
   an actuator coupled to the surgical machine, the actuator including
      a waveform control coupled to the surgical machine and activated when the surgical machine produces the first output;
      a compressor having a pneumatic input and a pneumatic output;
      an accumulator coupled to the compressor to receive the pneumatic output;
      a pressure sensor for sensing the pressure in the accumulator; and
      a valve coupled to the accumulator and the waveform control; and
   a surgical cutter coupled to the valve by a tubing.

8. A system as in claim 7, wherein the valve outputs a pressure waveform.

9. A system as in claim 8, wherein the pressure waveform has a variable pulse width.

10. A system as in claim 9, wherein the waveform control controls the pulse width of the pressure waveform as a function of a desired frequency and the pressure of the accumulator.

11. A system as in claim 7, further comprising a control and display device coupled to the waveform control, the control and display device having a plurality of input mechanisms and producing an output signal based on the inputs received through the input mechanisms.

12. A system as in claim 7, wherein said first output is pneumatic.

13. A system as in claim 7, wherein said first output is electrical.

14. A system as in claim 7, further comprising a controller coupled to the compressor and the pressure sensor, the controller operable to supply power to the compressor at a rate that is a function of the difference between the pressure in the accumulator and a predetermined pressure.

15. A pneumatic surgical cutting system comprising:
   a surgical machine operable to produce a first output;
   an actuator coupled to the surgical machine, the actuator including
      a waveform control coupled to the surgical machine and activated when the surgical machine produces the first output;
      a compressor having a pneumatic input and a pneumatic output;
      an accumulator coupled to the compressor to receive the pneumatic output;
      a pressure sensor for sensing the pressure in the accumulator; and
      a valve coupled to the accumulator and the waveform control;

a surgical cutter coupled to the valve by a tubing;

a second accumulator;

a connection between the second accumulator and the valve;

a connection between the second accumulator and the pneumatic input of the compressor; and a connection between the second accumulator and the atmosphere.

16. A system as in claim 15, wherein said connection between the second accumulator and the atmosphere includes a sound-absorber.

17. A system as in claim 15, wherein the valve is arranged such that the surgical cutter is alternately coupled to either the first accumulator or the second accumulator.

18. A surgical cutter assembly comprising:

a tubular outer member, being substantially rigid, having a proximal end and a distal end;

a cutting port, having a cutting edge, disposed near the distal end of the tubular outer member;

a tubular inner member, being substantially resilient, having a proximal end and a distal end, having an outer radius substantially less than the inner radius of said tubular outer member, wherein the distal end the tubular inner member is circularly flared to an outer radius which approximates the inner radius of said tubular outer member and wherein a cutting edge is formed on the distal end of the tubular inner member, said tubular inner member being disposed approximately coaxially within said tubular outer member;

driving means coupled to the proximal end of said inner member, operable to impart an axial reciprocating motion to said inner member; and a housing coupled to the proximal end of said outer member, wherein said driving means and tubular inner member are disposed in a fixed relationship to said tubular outer member;

said surgical cutter assembly having constructional features that cause the cutting edge of the tubular inner member to be resiliently biased against the inner surface of the tubular outer member along the side wherein the cutting port is disposed.

19. A surgical cutter assembly as in claim 18, wherein said constructional features include a bend in said tubular inner member.

20. A surgical cutter assembly as in claim 19, wherein said driving means is operable by pneumatic pressure.

21. A surgical cutter assembly as in claim 20, wherein said driving means is operable by a pneumatic pressure of approximately 13 psi or less.

22. A surgical cutter assembly as in claim 20, wherein said tubular inner member has a wall thickness of between 0.002 inches and 0.003 inches.

23. A surgical cutter assembly as in claim 19, wherein said tubular inner member has a wall thickness of between 0.002 inches and 0.003 inches.

24. A surgical cutter assembly as in claim 18, wherein said constructional features include a bend in said tubular outer member.

25. A surgical cutter assembly as in claim 18, wherein said driving means is operable by pneumatic pressure.

26. A surgical cutter assembly as in claim 25, wherein said driving means is operable by a pneumatic pressure of approximately 13 psi or less.

27. A surgical cutter assembly as in claim 18, wherein said tubular inner member has a wall thickness of between 0.002 inches and 0.003 inches.

28. A cutting system comprising:

an actuator providing a pressure pulse train having a variable pulse width, the actuator having a pressure source having a real-time pressure; and a waveform control that controls the pulse width of the pressure pulse train as a function of the desired frequency and the real-time pressure of the pressure source;

a pneumatically operated cutter assembly having a tubular outer member having a distal end, an inner radius, an outer radius and an inner surface, wherein a cutting port is disposed on a side of the tubular outer member near the distal end; and a resilient tubular inner member having a distal end and having an outer radius substantially less than the inner radius of the tubular outer member, wherein the distal end is flared to an outer radius which approximates the inner radius of said outer member and wherein a cutting edge is formed on the distal end, said tubular inner member being bent so as to resiliently bias the cutting edge of the tubular inner member against the inner surface of the tubular outer member along the side wherein the cutting port is disposed; and a tubing disposed between the actuator and the cutter assembly.

29. A cutting system as in claim 28, wherein the pulse width of the pressure pulse train is controlled such that the peak pressure of the pressure waveform at the juncture of the tubing with the cutter is at a predetermined level.

30. A cutting system as in claim 29, wherein said predetermined level is at or slightly above the level necessary to operate the cutter.

31. A cutting system as in claim 30, wherein said predetermined level is about 13 psi or less.

32. A cutting system as in claim 30, wherein the minimum pressure of the pressure waveform at the juncture of the tubing with the cutter is no greater than the pressure level necessary to permit the cutter blade to retract, when the frequency of the pressure pulse train is 900 pulses per minute or less.

33. A cutting system as in claim 30, wherein the minimum pressure of the pressure waveform at the juncture of the tubing with the cutter is no greater than the pressure level necessary to permit the cutter blade to retract, when the frequency of the pressure pulse train is 1500 pulses per minute or less.

34. A surgical cutter assembly comprising:

a tubular outer member, being substantially rigid, having a proximal end and a distal end;

a cutting port, having a cutting edge, disposed near the distal end of the tubular outer member;

a tubular inner member, being substantially resilient, having a proximal end and a distal end, having an outer radius substantially less than the inner radius of said tubular outer member, wherein the distal end is flared to an outer radius which approximates the inner radius of said tubular outer member and wherein a cutting edge is formed on the distal end, said tubular inner member being disposed approximately coaxially within said tubular outer member;

pneumatically operated driving means coupled to the proximal end of said inner member, operable to impart an axial reciprocating motion to said inner member, said means being operable by a pneumatic pressure of approximately 13 psi or less; and a housing coupled to the proximal end of said outer member, wherein said driving means and inner member are disposed in a fixed relationship to said outer member;

said surgical cutter assembly having constructional features, which cause the cutting edge of the tubular inner member to be resiliently biased against the inner surface of the tubular outer member along the side wherein the cutting port is disposed.

35. A surgical cutter assembly as in claim 34, wherein said constructional features comprise a bend in said tubular inner member.

36. A surgical cutter assembly as in claim 34, wherein said constructional features comprise a bend in said tubular outer member.

37. A surgical cutter assembly as in claim 34, wherein said tubular inner member has a wall thickness of between 0.002 inches and 0.003 inches.

* * * * *